United States Patent [19]
DeHaven-Hudkins et al.

[11] Patent Number: 5,455,248
[45] Date of Patent: Oct. 3, 1995

[54] SUBSTITUTED 6,11-ETHANO-6,11-DIHYDROBENZO[B]QUINOLIZINIUM SALTS, AND COMPOSITIONS AND METHOD OF USE THEREOF

[75] Inventors: Diane L. DeHaven-Hudkins, West Pikeland Township, Chester County; William G. Earley, Lower Providence Township, Montgomery County; Virendra Kumar, Tredyffrin Township, Chester County; John P. Mallamo, Uwchlan Township, Chester County; Matthew S. Miller, Lower Makefield Township, Bucks County; Chakrapani Subramanyam, Towamencin Township, Montgomery County, all of Pa.

[73] Assignee: Sterling Winthrop Inc., New York, N.Y.

[21] Appl. No.: 121,810

[22] Filed: Sep. 14, 1993

[51] Int. Cl.⁶ .................................................. A61K 31/47
[52] U.S. Cl. ........................... 514/289; 546/14; 546/15; 546/74; 546/283
[58] Field of Search ............................ 514/289; 546/74, 546/15

[56] References Cited

U.S. PATENT DOCUMENTS 3,517,073   6/1970   Fields .

OTHER PUBLICATIONS

Fields, et al., J Org. Chem. 1968, 33(1), 390–395.
Fields and Regan, J. Org. Chem. 1971, 36(20), 2986–2990.
Fields and Regan, J. Org. Chem. 1971, 36(20), 2991–2994.
Fields, J. Org. Chem. 1971, 36(20), 3002–3005.
Westerman and Bradsher, J. Org. Chem. 1971, 36(7), 969–970.
Bradsher and Day, J. Het. Chem. 1973, 10, 1031–1033.
Fields and Regan, J. Org. Chem. 1970, 35(6), 1870–1875.
Fields et al., J. Org. Chem. 1971, 36(20), 2995–3001.
Fields and Miller, J. Het Chem. 1970, 7, 91–97.
Bradsher and Stone, J. Org. Chem. 1968, 33(2), 519–523.
Bradsher and Solomons, J. Am. Chem. Soc. 1958, 80, 933–934.
Bradsher and Stone, J. Org. Chem. 1969, 34(6), 1700–1702.
Burnham and Bradsher, J. Org. Chem. 1972, 37(3), 355–358.
Parham et al., J. Org. Chem. 1972, 37(3), 358–362.
Bradsher et al., J. Am. chem. Soc. 1977, 99(8), 2588–2591.
Bradsher et al., J. Org. Chem. 1978, 43(5), 822–827.
Westerman and Bradsher, J. Org. Chem. 1978, 43(15), 3002–3006.
Westerman and Bradsher, J. Org. Chem. 1979, 44(5), 727–733.
Bradsher et al., J. Org. Chem. 1979, 44(8), 1199–1201.
Hart et al., Tetrahedron Letters 1975, 52, 4639–4642.

*Primary Examiner*—Donald G. Daus
*Attorney, Agent, or Firm*—Michael D. Alexander; Paul E. Dupont

[57] ABSTRACT

Substituted 6,11-ethano-6,11-dihydrobenzo[b]quinolizinium salts, pharmaceutical compositions containing them, and methods for the treatment or prevention of neurodegenerative disorders or neurotoxic injuries utilizing them.

16 Claims, No Drawings

SUBSTITUTED 6,11-ETHANO-6,11-DIHYDROBENZO[B] QUINOLIZINIUM SALTS, AND COMPOSITIONS AND METHOD OF USE THEREOF

BACKGROUND OF THE INVENTION

Field of the Invention

The invention relates to substituted 6,11-ethano-6,11-dihydrobenzo[b]quinolizinium salts, to compositions containing the same, and to the method of use thereof in the treatment or prevention of neurodegenerative disorders or neurotoxic injuries.

(b) Information Disclosure Statement

Fields, U.S. Pat. No. 3,517,073 issued Jun. 23, 1970, discloses compounds of the formula:

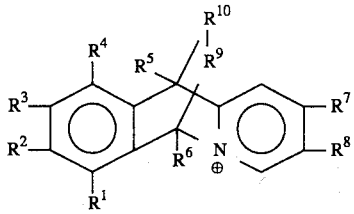

wherein each of $R^1$, $R^2$, $R^3$ and $R^4$ when taken separately, is hydrogen, lower alkyl, lower aryl, lower acyloxy, lower alkoxy, nitro, halogen, lower acylamino, di(lower alkyl) amino; one group of $R^1$ and $R^2$, $R^2$ and $R^3$, and $R^3$ and $R^4$, preferably $R^1$ and $R^2$, and $R^3$ and $R^4$, each group when taken together, represents a fused ring system containing up to three 6- member carbocyclic and nitrogen-containing heterocyclic rings at least one of which is an aromatic ring, and having no more than two nuclear nitrogens in any ring, which may be unsubstituted or substituted with one or more of the substituents defined by $R^1$, $R^2$, $R^3$ and $R^4$; each of $R^5$ and $R^6$, when taken separately is hydrogen, lower alkyl or lower aryl; each of $R^7$ and $R^8$, when taken separately, is hydrogen; $R^7$ and $R^8$, when taken together, represent a fused ring system as defined hereinbefore; $R^9$, when taken individually, is methylene or lower alkyl, lower aryl, lower alkenyl, halogen, or cyano substituted methylene; $R^{10}$, when taken individually, is a protected carbonyl group; $R^9$ and $R^{10}$, when taken together, represent a fused aromatic carbocyclic or heterocyclic ring system, whose valence bonds are from adjacent carbons, containing up to three 6-membered carbocyclic and nitrogen-containing heterocyclic rings having no more than two nitrogens in any ring and which may be substituted with one or more of the substituents defined by $R^1$, $R^2$, $R^3$ and $R^4$. Among the compounds specifically disclosed are 12,12-diethoxy-11-methyl-9,10-ethano-9,10-dihydro-4a-azoniaanthracene perchlorate and 9,10-(O-benzeno)-9,10-dihydro-5-methyl-4a-azoniaanthracene perchlorate. Also disclosed are compounds of the formula:

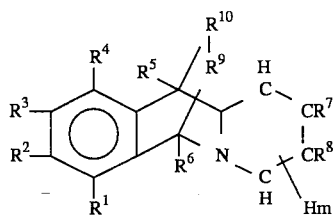

wherein $R^1$–$R^{10}$ are as defined above and m is an odd integer having a value of from 1 to 5, inclusive. Among the compounds specifically disclosed are 12,12-diethoxy-11-methyl-9,10-ethano-4a-aza-1,2,3,4,4a,9,9a,10-octahydroanthracene perchlorate acid salt, 9,10-(O-benzeno)-5-methyl-4a-aza-1,2,3,4,4a,9,9a,10octahydroanthracene and 12,12-diethoxy-9,10-ethano-11-bromo-4a-aza-1,2,3,4, 4a,9, 9a,10-octahydroanthracene. The above-described compounds are disclosed as being intermediates in the synthesis of 2-napthol derivatives and various anthracene derivatives.

Fields et al., J. Org. Chem. 1968, 33(1), 390–395, disclose a series of sixteen Diels-Alder adducts prepared from a 4a-azoniaanthracene ion and various dienophiles. Among the compounds specifically disclosed are 12-ethyl,12-hydroxymethyl and 12-ethylene-9,10-dihydro-4a-azonia-9,10-ethanoanthracene bromides; 12-phenyl-12-(4-morpholinyl), 12-methyl-12-(1methylethylene), 12,-12-diethoxy-11-bromo and 12-diethylamino-11-phenyl-9,10-dihydro-4a-azonia9,10-ethanoanthracene perchlorates, as well as 9,10 [1',2']cyclopentyl and 9,10-[2',3']tetrahydropyranyl-9,10-dihydro-4a-azoniaanthracene perchlorates. No utility is disclosed for these compounds.

Fields and Regan, J. Org. Chem. 1971, 36(20), 2986–2990, disclose compounds of the formula:

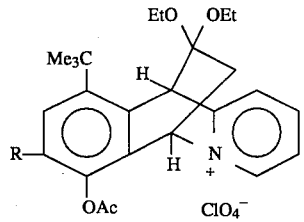

wherein R is H, Br, or OAc, as intermediates in the synthesis of substituted 8-tert-butyl-1-(2-pyridyl)napthalenes.

Fields and Regan, J. Org. Chem. 1971, 36(20), 2991–2994, disclose compounds of the formula:

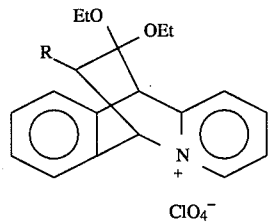

wherein R is H, $CH_3$, $C_6H_5$, or Br, as intermediates in the synthesis of 2-pyridylnapthols.

Fields, J. Org. Chem. 1971, 36(20), 3002–3005, discloses a series of substituted 12,12-diethoxy-9,10-ethano-9,10-dihydro-4a-azoniaanthracenes and the corresponding derivatives wherein the pyridinium moiety is partially or completely reduced, as intermediates in the synthesis of substituted 2-napthols. Among the compounds specifically disclosed is 12,12-diethoxy-5,11-dimethyl9,10-ethano-9,10-dihydro-4a-azoniaanthracene perchlorate. Also disclosed is a series of substituted 9,10-(O-benzeno)-9,10-dihydro-4a-azoniaanthracenes and the corresponding derivatives wherein the pyridinium moiety is partially or completely reduced, as intermediates in the synthesis of substituted anthracenes. Among the compounds specifically disclosed is 9,10-(O-benzeno)-9,10-dihydro-4a-azoniaanthracene perchlorate.

Westerman and Bradsher, J. Org. Chem. 1971, 36(7), 969–970, disclose compounds of the formula:

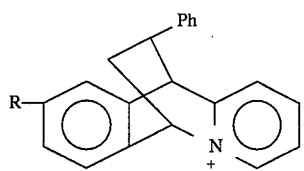

wherein R is $CH_3$, $CH(CH_3)_2$, H, F, I, Cl, Br, $CO_2H$, $CO_2CH_3$, or $NO_2$. No utility is disclosed for these compounds.

Bradsher and Day, J. Her. Chem. 1973, 10, 1031–1033, disclose four Diels-Alder adducts prepared from acridizinium perchlorate and cyclopentadiene, methyl vinyl ether, norbornadiene and maleic anhydride. No utility is disclosed for these compounds.

Fields and Regan, J. Org. Chem. 1970, 35(6), 1870–1875, disclose compounds of the formula:

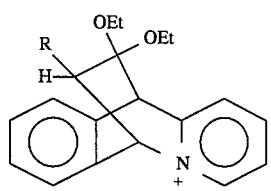

wherein R is H, $CH_3$ or $C_6H_5$. Also specifically disclosed are 9,10-dihydro-12,12-dimethoxy-11,11-dimethyl-4a-azonia-9,10-ethanoanthracene perchlorate and 9,10-dihydro-9,11-dimethyl-12,12-diethoxy-4a-azonia-9,10-ethanoanthracene perchlorate. The compounds are said to be intermediates in the synthesis of 9,10-dihydro-12-oxo-4a-azonia-9,10-ethanoanthracenes.

Fields et al., J. Org. Chem. 1971, 36(20), 2995–3001, disclose 9,10-dihydro-4a-azonia-9,10-O-benzenoanthracene perchlorate and several analogs as intermediates in the synthesis of various 9-(2-pyridyl)anthracenes.

Fields and Miller, J. Het. Chem. 1970, 7, 91–97, disclose a compound of the formula:

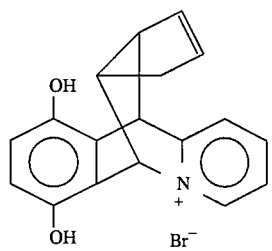

as an intermediate in the synthesis of the corresponding 5,8-dione salt.

Bradsher and Stone, J. Org. Chem. 1968, 33(2), 519–523, disclose a series of Diels-Alder adducts prepared from an acridizinium ion and maleic anhydride, maleate esters, fumarate esters and various para-substituted styrenes in which the para substituent is H, $CH_3$, $OCH_3$ or $NO_2$. No utility is disclosed for these compounds. A substantially similar disclosure for the preparation of Diels-Alder adducts from acridizinium bromide and maleic anhydride, maleate or fumarate esters can be found in Bradsher and Solomons, J. Am. Chem. Soc. 1958, 80, 933–934.

Bradsher and Stone, J. Org. Chem. 1969, 34(6), 1700–1702, disclose compounds of the formula:

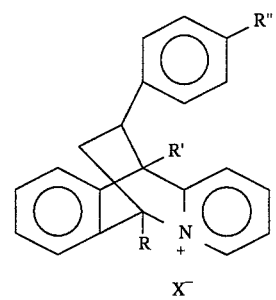

wherein R is H, or $CH_3$; R' is H, or $CH_3$; R" is $OCH_3$, $CH_3$, H, or $NO_2$; and $X^-$ is perchlorate; without an indication of utility. Also disclosed are the Diels-Alder adducts obtained from acridizinium perchlorate and diethyl maleate, diethyl fumarate or dimethyl maleate, without an indication of utility.

Burnham and Bradsher, J. Org. Chem. 1972, 37(3), 355–358, disclose compounds of the formula:

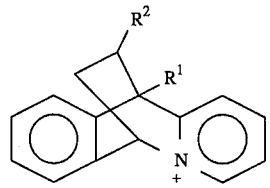

wherein $R^1$ is Ph, and $R^2$ is OEt; or $R^1$ is H, and $R^2$ is OEt, OBu, OAc, N-carbazolyl or 1-pyrrolidin-2-one, without an indication of utility.

Parham et al., J. Org. Chem. 1972, 37(3), 358–362, disclose compounds of the formula:

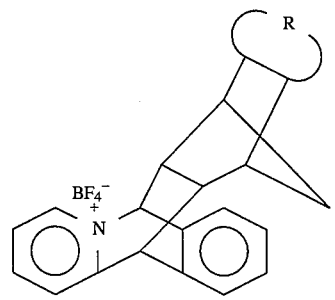

wherein R is $H_2$, $(CH_2)_3$, C(O)NHC(O), $C(O)N(CH_3)C(O)$, C(O)OC(O), $CH_2OCH_2$, or $CH_2NH_2^+CH_2$, without an indication of utility.

Bradsher et al., J. Am. Chem. Soc. 1977, 99(8), 2588–2591, disclose compounds of the formula:

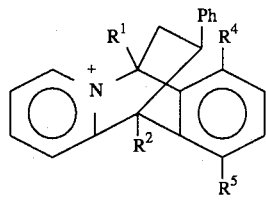

wherein: $R^1=R^2=R^4=R^5=H$; $R^1=Me$, and $R^2=R^4=R^5=H$; $R^1=R^4=R^5=H$, and $R^2=Me$; and $R^1=H$, and $R^2=R^4=R^5=Me$. No utility is disclosed for these compounds.

Bradsher et al., J. Org. Chem. 1978, 43(5), 822–827, disclose compounds of the formula:

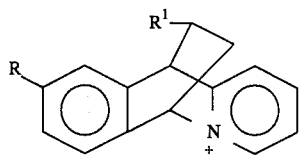

wherein: $R^1$ is OEt and R is Me, H, F, Cl, $CO_2Me$ or $NO_2$; $R^1$ is O-Ph-p-X, wherein X is $CH_3$, $OCH_3$, H, $C(O)CH_3$, or $NO_2$, and R is hydrogen; and $R^1$ is N-carbazolyl and R is hydrogen. No utility is disclosed for these compounds.

Westerman and Bradsher, J. Org. Chem. 1978, 43(15), 3002–3006, disclose a series of Diels-Alder adducts prepared from an acridizinium ion and various unsymmetrical alkenes, without an indication of utility. Among the compounds specifically disclosed are 6,11[2',3']indanyl-6,11-dihydroacridizinium tetrafluoroborate, and 12-phenyl-13-(2-pyridyl)-6,11-dihydro-6,11-ethanoacridizinium tetrafluoroborate.

Westerman and Bradsher, J. Org. Chem. 1979, 44(5), 727–733, disclose a series of Diels-Alder adducts prepared from a substituted or unsubstituted acridizinium cation and various polarizable alkenes without an indication of utility. Among the compounds specifically disclosed are 12,12-diphenyl-6,11-dihydro-6,11-ethanoacridizinium perchlorate or bromide, 9-methyl-6,11[2'3']indanyl-6,11-dihydroacridizinium tetrafluoroborate, and 7,10-dimethyl-12-phenyl-12-(4-morpholinyl), 9-methyl-12-phenyl-12-(4-morpholinyl), 12-(2-pyridyl), and 9-methyl-12-(2-pyridyl)-6,11-dihydro-6,11-ethanoacridizinium tetrafluoroborates.

Bradsher et al., J. Org. Chem. 1979, 44(8), 1199–1201, disclose a series of Diels-Alder adducts prepared from a substituted or unsubstituted acridizinium ion and cyclopropene or 1-methylcyclopropene, without an indication of utility.

Hart et al., Tetrahedron Letters 1975, 52, 4639–4642, disclose a compound of the formula:

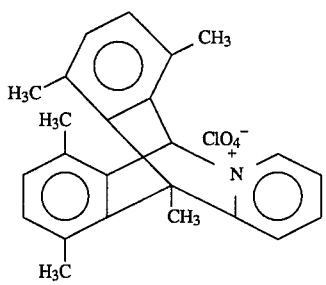

as an intermediate in the synthesis of 1,4,5,8,9-pentamethylanthracene.

SUMMARY OF THE INVENTION

The invention relates to compounds of the Formula I:

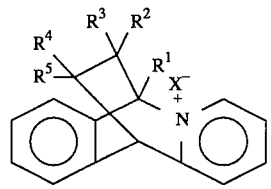

wherein:
$R^1$ is hydrogen, or lower-alkyl;
$R^2$ is hydrogen, or lower-alkyl;
$R^3$ is hydrogen, or lower-alkyl; or
$R^2$ and $R^3$ together are lower-alkylidene;
$R^4$ is hydrogen, lower-alkyl, lower-alkenyl, lower-alkoxy-lower-alkyl, cycloalkyl, hydroxylower-alkyl, or lower-alkynyl;
$R^5$ is hydrogen, lower-alkyl, lower-alkenyl, cycloalkyl, hydroxylower-alkyl, lower-alkoxy-lower-alkyl, or lower-alkynyl; or
$R^4$ and $R^5$ together form a lower-alkylidene, cycloalkyl, or adamantanyl group; and
$X^-$ is an anion;
or a stereoisomer thereof; with the following provisos:
(a) when $R^1, R^2$, and $R^3$ are hydrogen; $R^4$ is methyl; and $X^-$ is $Br^-$, $Cl^-$, or $ClO_4^-$, $R^5$ cannot be isopropenyl; b) when $R^1, R^2$, and $R^3$ are hydrogen; $R^5$ is methyl; and $X^-$ is $Br^-$, $Cl^-$, or $ClO_4^-$, $R^4$ cannot be isopropenyl; c) $R^1, R^2, R^3, R^4$ and $R^5$ cannot all simultaneously be hydrogen; and d) when $R^1, R^2$, and $R^3$ are hydrogen; $X^-$ is $Br^-$, and either, $R^4$ or $R^5$, but not both, is hydrogen; then either $R^4$ or $R^5$ cannot be ethenyl, hydroxymethyl, or ethyl.

The compounds of Formula I bind to the PCP receptor and are thus useful in the treatment or prevention of neurodegenerative disorders, or neurotoxic injuries.

Preferred compounds of Formula I above are those wherein:
$R^1$ is hydrogen, or methyl; $R^2$ is hydrogen, methyl, or tert-butyl; $R^3$ is hydrogen, methyl or tert-butyl; or $R^2$ and $R^3$ together are isopropylidene; and $R^4$, $R^5$ and $X^-$ are as defined hereinabove.

Particularly preferred compounds of the Formula I above are those wherein $R^4$ is hydrogen, methyl, isopropyl, tert-butyl, isopropenyl, isobutenyl, methoxymethyl, cyclopropyl, hydroxymethyl, ethoxymethyl, or ethynyl; $R^5$ is hydrogen, methyl, isopropyl, tert-butyl, isopropenyl, isobutenyl, cyclopropyl, hydroxymethyl, ethoxymethyl, or ethynyl; or $R^4$ and $R^5$ together form a isopropylidene, cyclobutyl, or adamantanyl group; $X^-$ is an anion; and $R^1$, $R^2$ and $R^3$ are as defined directly above.

The invention further relates to pharmaceutical compositions which comprise a compound of the Formula I:

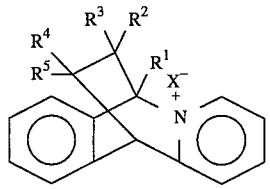

wherein:

$R^1$ is hydrogen, or lower-alkyl;

$R^2$ is hydrogen, or lower-alkyl;

$R^3$ is hydrogen, or lower-alkyl; or $R^2$ and $R^3$ together are lower-alkylidene;

$R^4$ is hydrogen, lower-alkyl, lower-alkenyl, lower-alkoxy-lower-alkyl, cycloalkyl, hydroxylower-alkyl, or lower-alkynyl;

$R^5$ is hydrogen, lower-alkyl, lower-alkenyl, cycloalkyl, hydroxylower-alkyl, lower-alkoxy-lower-alkyl, or lower-alkynyl; or $R^4$ and $R^5$ together form a lower-alkylidene, cycloalkyl, or adamantanyl group; and $X^-$ is an anion;

or a stereoisomer thereof; together with a pharmaceutically acceptable carrier, adjuvant, diluent, or vehicle; with the proviso that $R^1,R^2,R^3,R^4$ and $R^5$ cannot all simultaneously be hydrogen; further provided that when $R^1,R^2$, and $R^3$ are hydrogen, $X^-$ is $Br^-$ and either $R^4$ or R5, but not both, is hydrogen, then either $R^4$ or $R^5$ cannot be ethyl.

The invention further relates to a method for the treatment or prevention of neurodegenerative disorders, or neurotoxic injuries which comprises administering to a patient in need of such treatment an effective amount of a compound of the formula:

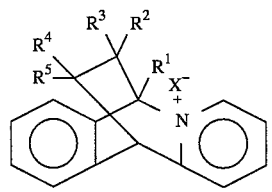

wherein:

$R^1$ is hydrogen, or lower-alkyl;

$R^2$ is hydrogen, or lower-alkyl;

$R^3$ is hydrogen, or lower-alkyl; or $R^2$ and $R^3$ together are lower-alkylidene;

$R^4$ is hydrogen, lower-alkyl, lower-alkenyl, lower-alkoxy-lower-alkyl, cycloalkyl, hydroxylower-alkyl, or lower-alkynyl;

$R^5$ is hydrogen, lower-alkyl, lower-alkenyl, cycloalkyl, hydroxylower-alkyl, lower-alkoxy-lower-alkyl, or lower-alkynyl; or $R^4$ and $R^5$ together form a lower-alkylidene, cycloalkyl, or adamantanyl group; and $X^-$ is an anion;

or a stereoisomer thereof; with the proviso that $R^1,R^2,R^3$, $R^4$ and $R^5$ cannot all simultaneously be hydrogen; further provided that when $R^1,R^2$, and $R^3$ are hydrogen, $X^-$ is $Br^-$ and either $R^4$ or $R^5$, but not both, is hydrogen, then either $R^4$ or $R^5$ cannot be ethyl.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term halogen or halide as used herein means bromine, chlorine, iodine, or fluorine.

The term lower-alkylidene as used herein means linear or branched hydrocarbon chains having one to about four carbon atoms and thus includes methylidene, ethylidene, propylidene, isopropylidene, sec-butylidene and the like.

The term cycloalkyl as used herein means $C_3$ to $C_7$ saturated monocyclic hydrocarbon residues and thus includes cyclopropyl, cyclobutyl, cyclopentyl, cyclohexyl and cycloheptyl.

The term lower-alkynyl as used herein means linear or branched unsaturated radicals having two to about four carbon atoms and thus includes ethynyl, 1-propynyl, 2-propynyl, 1-methyl-2-propynyl, 2-butynyl and the like.

The term lower-alkenyl as used herein means linear or branched unsaturated radicals having two to about four carbon atoms and thus includes ethenyl, 1-propenyl, 2-propenyl, isopropenyl, 1-methyl-2-propenyl, 2-butenyl, isobutenyl and the like.

The term hydroxylower-alkyl as used herein means lower-alkyl as defined above substituted by hydroxy and thus includes hydroxymethyl, 1-hydroxy-1-methylethyl, 2-hydroxyethyl, 2-hydroxy-2-methylpropyl and the like.

The term anion ($X^-$) as used herein means the anion of an organic acid (includes anions or organic monoacids, as well as monoanions of organic diacids) which is at least as strong as acetic acid, and thus includes anions of such acids as acetic acid, methanesulfonic acid, toluenesulfonic acid, e.g. p-toluenesulfonic acid, trifluoromethanesulfonic acid, (−)-dibenzoyl-L-tartaric acid [(−)-DBT], (+) dibenzoyl-D-tartaric acid [(+)-DBT], and the like; or it means an inorganic acid anion such as chloride, bromide, perchlorate, $PF_6^-$ and the like, preferably chloride.

The numbering system used throughout the specification is shown in the ring system which is illustrated below. This ring system is usually named in the chemical literature as a 6,11-ethano-6,11-dihydrobenzo[b]quinolizinium salt or

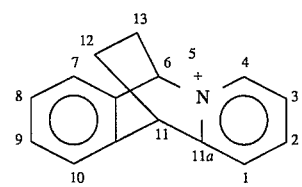

a 6,11-dihydro-6,11-ethanoacridizinium salt. It should be noted, however, that in some of the earlier chemical literature references (see references cited in Information Disclosure Statement) this ring system was numbered as shown below, and was named as a 9,10-ethano-9,10-dihydro-4a-azoniaanthracene, or a 9,10-dihydro-4a-azonia-9,10-ethanoanthracene. Throughout this specification,

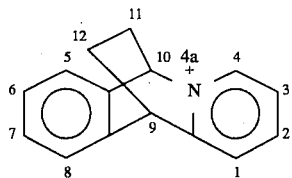

however, we will use the former numbering system, and we will name the compounds as substituted 6,11-ethano-6,11-dihydrobenzo[b]quinolizinium salts.

The synthesis of the compounds of the invention may be outlined as shown in Scheme A:

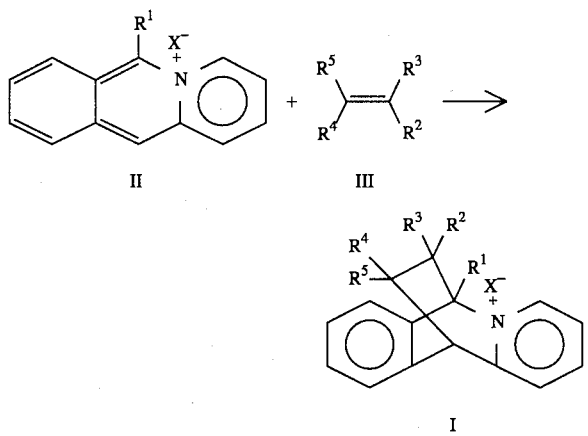

A suitably substituted benzo[b]quinolizinium salt (II) in an appropriate organic solvent, e.g. acetonitrile or nitromethane, is treated with at least one molar equivalent of a suitably substituted olefin (III), at a temperature in the range of about 50° C. up to the boiling point of the solvent used, to afford the compounds of Formula I.

If desired, the compounds of Formula I can be converted into other compounds of Formula I which possess various different anion groups (X⁻) by a) treating a compound of Formula I with an aqueous solution of the alkali metal salt of an inorganic acid anion or an organic acid anion; M⁺X⁻, wherein the acid of the salt used is a stronger acid than the corresponding acid of the initial acid anion (X⁻), and wherein M⁺ is an alkali metal, preferably the alkali metal salt of an inorganic acid anion; to produce compounds of the Formula I wherein X⁻ is various other anion groups (X⁻); b) if compounds of the Formula I wherein X⁻ is chloride (Cl⁻) are desired, by passing a compound of the Formula I wherein X⁻ is other than Cl⁻ through a Dowex®1X2-200 ion-exchange resin (Dowex®-1-chloride) column eluting with water to provide the compounds of Formula wherein X⁻ is Cl⁻; or c) by passing a compound of the Formula I through a suitable ion-exchange resin column (prepared, for example, by treating Dowex®1X2-200 ion-exchange resin with a suitable organic acid or inorganic acid) to provide various compounds of Formula I wherein X⁻ is other than Cl⁻, $ClO_4^-$ or $PF_6^-$.

It will be appreciated that the compounds of the Formula I can possess one or more asymmetric carbon atoms and are thus capable of existing in a number of stereoisomeric forms, e.g. enantiomers, diastereomers, and geometric isomers. Unless otherwise specified herein, the invention is intended to extend to each of these stereoisomeric forms, and to mixtures thereof, including the racemates. In some cases there maybe advantages, e.g. greater potency, to using a particular enantiomer when compared to the other enantiomer or the racemate in the treatment or prevention of neurodegenerative disorders or neurotoxic injuries, and such advantages can be readily determined by those skilled in the art. The different stereoisomeric forms may be separated one from the other by the methods described hereinbelow:

The diastereomers/geometric isomers can be separated by conventional procedures which are well known in the art of chemistry such as chromatography, fractional crystallization and the like. The separation of enantiomers can be accomplished by a) chiral chromatography; b) treating a racemic mixture of a compound of Formula I with the potassium salt of (+)-dibenzoyl-D-tartaric acid (K⁺[(+)-DBT]) to afford a compound of Formula I as the −[(+)-DBT] salt; fractional crystallization of the −[(+)-DBT]salt to afford a single diastereomer of the −[(+)-DBT] salt, and then conversion of the single diastereomer of the −[(+)-DBT] salt into various other non-chiral anions (X⁻) by following the procedures described hereinabove for the conversion of compounds of the Formula I into other compounds of the Formula I with various different anions (X⁻), to produce the compounds of the Formula I as a single enantiomer; or c) treating a racemic mixture of a compound of Formula I with the potassium salt of (−)-dibenzoyl-L-tartaric acid (K⁺[(−)-DBT]) to afford a compound of Formula I as the -[(−)-DBT] salt and then proceeding as described hereinabove in pan (b) to afford the compounds of Formula I as the other enantiomer.

The suitably substituted benzo[b]quinolizinium salts of the Formula II, which are required for the synthesis of the compounds of Formula I, are either known and can thus be prepared by procedures which are known in the art of chemistry (see for example, Bradsher and Parham, J. Org. Chem., 1963, 28, 83–85 and Bradsher and Parham, J. Her. Chem., 1964, 1, 121–124); or if they are novel they can be prepared by the procedures described in the art or those described hereinbelow and illustrated in Scheme B. At least one molar equivalent of an appropriately substituted benzyl halide (IV), wherein Z is

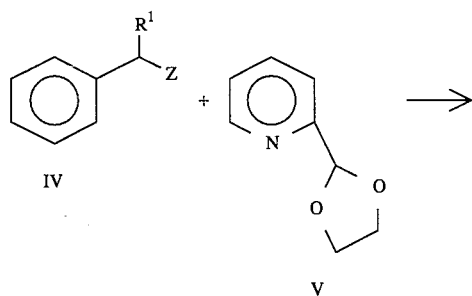

11

-continued
Scheme B

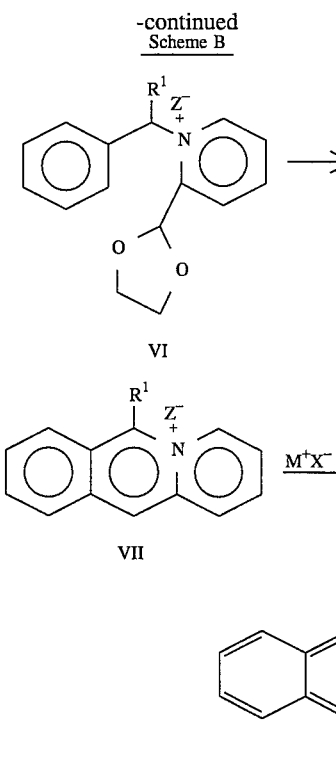

halogen, preferably bromine, is treated with one mole of 2-(1,3-dioxolan-2-yl) pyridine (V), in the presence of a suitable solvent, e.g. sulfolane, at a temperature of about room temperature up to the boiling point of the solvent used, to produce the pyridinium salt (VI). The pyridinium salt (VI) can then be treated with an excess of an acid, e.g. polyphosphoric acid, at a temperature in the range of about 40° C. up to the boiling point of the acid used, to produce the compounds of Formula VII (Formula II wherein $Z^-=X^-$=halogen). If desired, the compounds of Formula VII can be converted into the compounds of Formula II which passess various anion groups ($X^-$) other than halogen by treating the compounds of Formula VII with the alkali metal salt of an inorganic acid anion or an organic acid anion, $M^{30}$ $X^-$ wherein the acid of the salt used is a stronger acid than the corresponding acid of the initial acid anion.

The appropriately substituted olefin (III), the alkali metal salts of inorganic acid anions and organic acid anions ($M^+X^-$), benzyl halide (IV), and 2-(1,3-dioxolan-2-yl) pyridine (V) are commercially available, or they can be prepared by procedures known in the art, or by the procedures described hereinbelow.

The compounds of Formula I are quinolizinium salts in which it is preferred that the salts are pharmaceutically acceptable salts, that is, salts whose anions ($X^-$) are relatively innocuous to the animal organism in pharmaceutical doses of the salts, so that the beneficial properties inherent in the compounds of the Formula I are not vitiated by side effects .ascribable to the anions ($X^-$). In practicing the present invention it is convenient to use the anions ($X^-$) of organic acids such as methanesulfonic acid and toluenesulfonic acid, or the anions ($X^-$) of inorganic acids such as hydrobromic acid and hydrochloric acid. However, other appropriate pharmaceutically acceptable salts within the scope of the invention are those derived from the anions ($X^-$) of other organic acids, organic diacids, or inorganic acids.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected. The abbreviation E/PAW as used herein means a mixture of ethyl acetate and pyridine/acetic acid/water (55/20/25).

PREPARATION OF STARTING MATERIALS

Preparation 1

(a)

A reaction mixture of 24 g (0.159 mol) of 2-(1,3-dioxolan-2-yl)pyridine and 32 g (0.173 mol) of 1-bromoethylbenzene in 16 ml of sulfolane was allowed to stir under nitrogen and at room temperature for 36 hours. The reaction mixture containing crystalline solid was diluted with ethyl acetate, filtered, and the residual solid was washed with ethyl acetate and dried to afford 17.4 g (32.5%) of 1-(1-methyl)benzyl-2-(1,3-dioxolan-2-yl)pyridinium bromide. The filtrate was concentrated in vacuo to remove ethyl acetate and the residue was allowed to stir with ethyl acetate under nitrogen for 120 hours. The mixture was filtered, the residual solid was washed with ethyl acetate, and dried to yield an additional 13 g (24.3%) of 1-(1-methyl)benzyl-2-(1,3-dioxolan-2-yl)pyridinium bromide (Formula VI: $R^1$=CH$_3$;$Z^-$=Br$^-$).

(b)

A mixture of 3 g (8.9 mmol) of 1-(1-methyl)benzyl-2-(1, 3-dioxolan-2-yl)pyridinium bromide and 30 g of polyphosphoric acid was heated at 95° C. for 5 hours. The mixture was cooled to 40° C., cold water (75 mL) was added (temperature rose to 50° C.), additional cold water (75 mL) was added and the mixture was cooled to ambient temperature. Potassium hexafluorophosphate (5.0 g) was added to the aqueous solution and the precipitate which formed was collected by filtration, washed with water, then ether, to afford 2.6 g (86.8%) of 6-methylbenzo[b]quinolizinium hexafluorophosphate (Formula II: $R^1$=CH$_3$; $X^-$=PF$_6^-$).

Preparation 2

(a)

A reaction mixture of 200 g (1.25 mol) of diethyl malonate, 159.51 g (1.56 mol) of acetic anhydride, 108.9 g (1.87 mol) of acetone, and 25.5 g (0.187 mol) of zinc chloride placed in a 1000 ml round bottom flask was allowed to reflux for 20 hours. The reaction mixture was cooled, diluted with 200 ml of benzene, and the resulting mixture was washed with water (4×250 ml). The combined aqueous layer was extracted with benzene (2×50 ml) and the organic layers were combined. After removing benzene in vacuo, the mixture was distilled twice (Vigreux distilling column—10") to afford 111.8 g (44.7%—crude) of diethyl isopropylidenemalonate contains a trace of diethyl malonate), b.p. 80° C./0.5 mm.

(b)

To a mixture of 3.98 g (0.104 mol) of lithium aluminum hydride suspended in 50 ml of benzene at 60° C. was added in portions 10 g (49.9 mmol) of diethyl isopropylidenemalonate in 20 ml of benzene at a rate to maintain the reflux temperature and then the mixture was maintained at 60° C. with occasional heating. The reaction mixture was cooled to 0° C. and treated slowly with 30 g (93.1 mmol) of sodium sulfate decahydrate and water. The reaction mixture was filtered, the residue was washed with ether, and the organic layer was dried over sodium sulfate and filtered. The filtrate was concentrated in vacuo and the pale yellow liquid was distilled to afford 2.4 g (41.4%) of 1,1-dimethyl-2,2-di(hydroxymethyl)ethylene (Formula III: $R^2=R^3=CH_3; R^4=R^5=CH_2OH$), b.p. 85°–90° C./0.25 mm. The product solidified on standing.

(c)

To 20 ml of tetrahydrofuran cooled to 0° C. was added with stirring 2.15 g (18.7 mmol) of 1,1-dimethyl-2,2-di(hydroxymethyl)ethylene and 10.66 g (75 mmol) of methyl iodide, and then 1.12 g (46.7 mmol) of sodium hydride. The resulting mixture was allowed to react at room temperature for 1 hour. The reaction mixture was filtered, the filtrate was concentrated in vacuo, and 100 ml of ether and 15 ml of 10% HCl was added to the residue. The aqueous layer was extracted with ether (2×50 ml), the combined ethereal solution was dried over sodium sulfate and filtered. The solvent was removed in vacuo and a pale brown liquid was distilled to afford 2.2 g (81.8%) of 1,1-dimethyl-2,2di(methoxymethyl)ethylene (Formula III: $R^2=R^3=CH_3; R^4=R^5=CH_2OCH_3$), b.p. 70°–75° C./45mm.

Preparation 3

Benzo[b]quinolizinium bromide (508.5 g, 1.95 mol) (Bradsher and Parham, J. Org. Chem., 1963, 28, 83–85, Example VIIa) was dissolved in distilled water (5L) with heating and potassium hexafluorophosphate (367.2 g, 1.95 mol) in water (1.1L) was added in portions. After the addition was complete, the mixture was stirred at ambient temperature for 3 hours, then at 0° C. for 1 hour. The mixture was filtered and washed with cold water to afford 601 g (94.8%) of benzo[b]quinolizinium hexafluorophosphate. (Formula II: $R^1=H; X^-=PF_6^-$).

Preparation 4

To 1000 ml (1.7 mol) of tert-butyllithium in pentane cooled to −78° C. was added 56.7 g (0.566 mol) of 2,2-dimethyl-3,4-epoxybutane. When the addition was complete, the mixture was allowed to warm to room temperature, and then was allowed to reflux for 48 hours (during the reaction the solution turns yellow). The reaction mixture was cooled, ammonium chloride (20 g) was slowly added to the mixture, and an additional 40 ml of ammonium chloride solution was added in portions during a period of 40 minutes. The mixture was filtered, the aqueous layer was extracted with ether (2×100 ml), the combined organic layer was dried over sodium sulfate and filtered. The solvent was removed in vacuo and the product was distilled to afford 49.1 g (62%) of 1,2-di(tert-butyl)ethylene (Crandall and Lin, J. Am. Chem. Soc. 1967, 4527–4528) (Formula III: $R^3=R^4=C(CH_3)_3; R^5=H$), as a colorless liquid, b.p. 122°–135° C.

Preparation 5

To a suspension of methyltriphenylphosphonium bromide (68.08 g; 0.1906 mol) in 250 ml of tetrahydrofuran cooled to −10° C. was added 19 ml (0.1906 mol) of n-butyllithium in hexane followed by dicyclopropyl ketone (20 g, 0.18 mol) and the mixture was allowed to reflux for 2 hours. After adding an additional 50 ml of tetrahydrofuran, the reaction mixture was allowed to reflux for an additional 4½ hours.

The reaction mixture was cooled, filtered, the filtrate was concentrated (to 40 ml of volume), and 200 ml of hexane was added. The hexane layer was decanted, concentrated in vacuo, and the residue was purified by chromatography eluting with hexane to afford 8.63 g (45%) of 1,1-dicyclopropylethylene (Formula III: $R^2=R^3=H; R^4=R^5=$cyclopropyl).

Preparation 6

To a suspension of methyltriphenylphosphonium bromide (14 g; 39.17 mmol) in 100 ml of ether cooled to 0° C. under argon was added dropwise n-butyllithium (2.51 g; 39.17 mmol) in hexane (15.7 mml). An ice-bath was removed and the mixture was allowed to react at room temperature for 2 hours. After cooling the reaction mixture to 0° C., a suspension of 5.35 g (35.61 mmol) of 2-adamantanone in ether (25 ml) was added and the mixture was stirred at room temperature for 2 hours. Acetone was added to decompose the phosphonium salt, the reaction mixture was filtered and the residue was washed with ether. The combined organic layer was distilled in vacuo and the residue was redissolved in ether and cooled to 0° C. to yield 3.5 g (66.4%) of 2-methylene-adamantane (see J. Org. Chem. 1985, 54, 1375) (Formula III: $R^2=R^3=H; R^4$ and $R^5$ together are adamantanyl), as a low melting solid.

Preparation 7

Following a procedure similar to that described in preparation 2(c), there was obtained 2.8 g (68%) of 2,2-(diethoxymethyl) ethylene (Formula III: $R^2=R^3=H; R^4=R^5=CH_2OC_2H_5$) from 2-methylene-1,3-propane diol (2.5 g, 0.028 mol), 60% NaH (2.24 g, 0.056 mol), THF (25 mL) and ethyl iodide (8.73 g, 0.056 mol).

PREPARATION OF THE FINAL PRODUCTS

EXAMPLE 1

A reaction mixture of 2 g (7.1 mmol) of benzo[b]quinolizinium perchlorate and 2 ml of 1,1,2,2-tetramethylethylene in 40 ml of nitromethane placed in a sealed tube was heated at 130° C. for 24 hours. The reaction mixture was filtered to remove the solid precipitate and the solvent was removed in vacuo. A black foamy residue was dissolved in chloroform, filtered through supercel, and the solvent was removed in vacuo. The residual solid was crystallized from acetone to afford 215 mg (14 %) of 6,11-ethano-12, 12, 13,13-tetramethyl-6,11-dihydrobenzo[b]quinolizinium perchlorate (Formula I: $R^1=H; R^2=R^3=R^4=R^5=CH_3; X^-=ClO_4^-$), m.p.>280° C.

EXAMPLES 2 & 3

A reaction mixture of 10 g (40.3 mmol) of benzo[b]quinolizinium bromide and 6.62 g (80 mmol) of 2,3-dimethyl-1,3-butadiene in 100 ml of nitromethane was warmed to 60° C. and the resulting solution was heated at 100° C. The reaction mixture was cooled, filtered, and the solvent was concentrated in vacuo to yield a brown semi-solid (crude yield, 13.5 g). A brown solid was purified by chromatography on silica ethyl acetate/PAW (1.5/1) wherein PAW is pyridine/acetic acid/water (55/20/25) to ethyl acetate/PAW (1/1) to afford 1 g (15%) of 6,11-ethano-12-isopropenyl-12-methyl-6,11-dihydrobenzo[b]quinolizinium bromide (Example 2)(Formula I: $R^1=R^2=R^3=H;R^4=CH_3;R^5=CH_2=C(CH_3)—; X^-=Br^-$); m.p. 220°(d) and 1.2 g (18%) of 6,11-ethano-12-isopropenyl-12-methyl-6,11-dihydrobenzo[b]quinolizinium bromide (Example 3)(Formula I: $R^1=R^2=R^3=H;R^4=CH_2=C(CH_3)—;R^5=CH_3;X^-=Br^-$); m.p. 210°–16° C.).

EXAMPLE 4

Following a procedure similar to that described in Example 2, a reaction mixture of 3.3 g (15.2 mmol) of benzo[b]quinolizinium bromide and 2.2 g (15.2 mmol) of 1,1-dimethyl-2,2-dimethoxymethyl-ethylene in 25 ml of nitromethane was refluxed for 18 hours. The reaction mixture was cooled and filtered. The residue was redissolved in nitromethane, treated with activated charcoal, and filtered. The pale-orange colored organic mixture was concentrated in vacuo and the resulting residue was purified by chromatography over silica eluting with methanol:methylene chloride (1:9) followed by E/PAW (1.1:1). The solvent was removed in vacuo and the residue was treated with sodium perchlorate in water. The solid product was filtered, washed with water, decanted, and dried to afford 220 mg (7.6%; a pure single isomer) of 6,11-ethano-12-isopropenyl-12-methoxymethyl-6,11-dihydrobenzo[b]quinolizinium perchlorate (Formula I: $R^1=R^2=R^3=H; R^4=CH_2OCH_3;R^5=CH_2C(CH_3)—;X^-=ClO_4^-$).

EXAMPLE 5

Following a procedure similar to that described in Example 2, a reaction mixture of 6 g (19.6 mmol) of benzo[b]quinolizinium hexafluorophosphate and 6.44 g (7.8 mmol) of 2,3-dimethyl-butadiene dissolved in 150 ml of nitromethane was heated to reflux for 6 hours. The reaction mixture was cooled, filtered, and the filtrate was concentrated in vacuo. The solid residue was purified by chromatography over silica gel eluting with 9% methanol in methylene chloride. The above purified product in a minimum amount of methylene chloride was passed through 100 g of Dowex®1×2-200 eluting with water, and the solvent was concentrated in vacuo to yield a foamy solid product. The solid product was triturated with methylene chloride/ethyl acetate while warming and the solvent was decanted. The chloride salt was triturated in ethyl acetate and filtered to afford 3.7 g (63.6%) of 6,11-ethano-12-isopropenyl-12-methyl-6,11dihydrobenzo[b]quinolizinium chloride (as a 2:1 mixture of geometric isomers) (Formula I: $R^1=R^2=R^3=H;R^4=CH_3;R^5=CH_2—=C(CH_3)—;X^-=Cl^-$ and Formula I: $R^1=R^2=R^3=H;R^4=CH_2=C(CH_3)—;R^5=CH_3;X^-=Cl^-$), as an amorphous white solid, m.p. 85°–90° C.

EXAMPLES 6 & 7

By a process analogous to that of Example 2, 4.57 g (32.6 mmol) of 1,2-di-tert-butylethylene was added to 40 ml of nitromethane containing 5 g (16.3 mmol) of benzo[b]quinolizinium hexafluorophosphate. The reaction mixture was allowed to reflux for 48 hours, cooled, and filtered. The filtrate was concentrated and the residue was redissolved in ethyl acetate while heating. The solution was cooled, filtered, and the filtrate was concentrated in vacuo.

The above residue was purified by chromatography on silica gel eluting with E/PAW; (from 2/1 to 1/1) to yield the first fraction—isomer A and the second fraction—isomer B respectively. The first fraction was concentrated in vacuo, the residue was triturated with 100 ml of toluene, and the solvent was removed in vacuo to afford 330 mg (11.5%) of 6,11-ethano-12-tert-butyl13-tert-butyl-6,11-dihydrobenzo[b]quinolizinium hexafluorophosphate (Example 6)(Formula I: $R^1=R^2=R^5=H;R^3=R^4=C(CH_3)_3;X^-=PF_6^-$; isomer A), as an amorphous tan powder, m.p. 83°–90° C.

Similarly the second fraction was concentrated in vacuo, the residue was triturated with 100 ml of toluene, and the solvent was removed in vacuo to afford 299 mg (11.2%) of 6,11-ethano-12-tert-butyl-13-tert-butyl-6,11-dihydrobenzo[b]quinolizinium hexafluorophosphate (Example 7)(Formula I: $R^1=R^3=R^4=H;R^2=R^5=C(CH_3)_3;X^-=PF_6^-$; isomer B), as an amorphous tan powder, m.p. 87°–95° C.

EXAMPLE 8

By a process analogous to that of Example 2, 2.5 g (24 mmol) of 1,1-dicyclopropylethylene was added to 50 ml of nitromethane containing 4.5 g (16.1 mmol) of benzo[b]quinolizinium perchlorate. The reaction mixture was heated at 50°–60° C. for 80 minutes, to which 1 g of an additional 1,1-dicyclopropylethylene was added, and the reaction mixture was allowed to react at 60° C. for 24 hours. The mixture was cooled, concentrated, and the foamy residue was redissolved in hot ethyl acetate. The white precipitated solid was isolated and dried ( at 60° C., 0.01 mm) to afford 6.15 g (98.7%) of 6,11- ethano-12,12-dicyclopropyl-6,11-dihydrobenzo[b]-quinolizinium perchlorate (Formula I: $R^1=R^2=R^3=H;R^4=R^5=$cyclopropyl;$X^-=ClO_4^-$), as a white solid, m.p. 160°–62° C.

EXAMPLE 9

The above 6,11-ethano-12,12-dicyclopropyl-6,11-dihydrobenzo[b]quinolizinium perchlorate 5.27 g (13.6 mmol) in a minimum of methylene chloride was passed through 80 g of Dowex®1×2-200 eluting with water and the solvent was concentrated in vacuo. The solid product was triturated with 100 ml of toluene and the solvent was concentrated in vacuo. The resulting residue was triturated with hot ethyl acetate, filtered, and dried (35° C.) to afford 3.65 g(82.9%) of 6.11-ethano-12,12-dicyclopropyl-6,11-dihydrobenzo[b]quinolizinium chloride (Formula I: $R^1=R^2=R^3=H;R^4=R^5=$cyclopropyl;$X^-=Cl^-$), as a white powder, m.p. 64°–72° C.

EXAMPLE 10

(a)

Following a procedure similar to that described in Example 2, a reaction mixture of 1 g (3.56 mmol) of benzo[b]quinolizinium perchlorate and 0.5 g (7.2 mmol) of methylenecyclobutane in 20 ml of acetonitrile was allowed to reflux under argon for 3 days. The solvent was removed in vacuo to isolate a crude residue (1.3 g). The solid was recrystallized from acetonitrile to afford 750 mg (60%) of 6,11-ethano-12,12-(1'-spirocyclobutane)-6,11-dihydrobenzo-[b]quinolizinium perchlorate (Formula I: $R^1=R^2=R^3=H;R^4$ and $R^5$ together=cyclobutyl; $X^-=ClO_4^-$), as a light yellow solid.

(b)

The above purified perchlorate in a minimum amount of methylene chloride was passed through Dowex®1×2-200 eluting with water and the solvent was concentrated in vacuo to yield a foamy solid product (0.61 g). The solid product was recrystallized from methylene chloride/ether to afford 520 mg (85.3%) of 6,11-ethano-12,12-(1'-spirocyclobutane)-6,11-dihydrobenzo[b]-quinolizinium chloride (Formula I: $R^1=R^2=R^3=H;R^4$ and $R^5$ together=cyclobutyl;$X^-=Cl^-$), as a white solid, m.p. 310°–312° C.(d).

EXAMPLE 11

(a)

Following a procedure similar to that described in Example 2, a reaction mixture of 1.5 g (5.36 mmol) of benzo[b]quinolizinium perchlorate and 0.94 g (10.73 mmol) of 2-methylene-1,3-propanediol in 20 ml of acetonitrile was allowed to reflux under argon for 2 days. The solvent was removed in vacuo to isolate a crude syrup. The crude product was triturated with ethyl acetate/ether (1:1) and the resulting white solid was isolated to yield 1.8 g of 6,11-ethano-12,12-dihydroxymethyl-6,11-dihydrobenzo[b]quinolizinium perchlorate (Formula I: $R^1=R^2=R^3=H;R^4=R^5=CH_2OH;X^-=ClO_4^-$).

(b)

The above purified perchlorate (1.8 g) was passed through Dowex®1×2-200 during with water, and the solvent was concentrated in vacuo to yield a glass. The product was reprecipitated from isopropanol/isopropyl acetate to afford 1 g (68.75%) of 6,11-ethano-12,12-dihydroxymethyl-6,11-dihydrobenzo[b]quinolizinium chloride (Formula I: $R^1=R^2=R^3=H;R^4=R^5=CH_2OH;X^-=Cl^-$), as an amorphous powder.

EXAMPLE 12

Following a procedure similar to that described in Example 2, a reaction mixture of 0.52 g (1.52 mmol) of 6-methylbenzo[b]quinolizinium hexafluorophosphate and 2.5 g (30.4 mmol) of 2,3-dimethylbutadiene in 50 ml of nitromethane was allowed to reflux under nitrogen for 10 hours. The mixture was cooled, the solvent was removed in vacuo, and the residue was passed through silica gel eluting with 300 ml of 10% methanol in methylene chloride. The organic solvent was removed in vacuo and the residual product was passed through 50 g of Dowex®1×2-200 eluting with water. The eluents were combined and treated with 50 ml of 20% sodium perchlorate solution. The solid product was filtered, washed with ether, and air dried under diminished pressure for 72 hours to afford as a mixture of geometric isomers 6,11-ethano-6-methyl-12-isopropenyl-12-methyl-6,11-dihydrobenzo[b]quinolizinium perchlorate (Formula I: $R^1=CH_3;R^2=R^3=H;R^4=CH_3;R^5=CH_2=C—(CH_3)—;X^-=ClO_4^-$, and Formula I: $R^1=CH_3;R^2=R^3=H;R^4=CH_2=C—(CH_3)—;R^5=CH_3;X^-=ClO_4^-$), m.p. 120°–24° C.

EXAMPLES 13(a) and 13(b)

6,11-ethano-12-ethylene-6,11-dihydrobenzo[b]quinolizinium bromide as a 1/1 mixture of geometric isomers was purified by column chromatography (2×) on silica gel eluting with E/PAW (1/1) to afford fractions A and B.

The Fraction A was concentrated in vacuo and the residue was disolved in 50 ml of hot methylene chloride containing 0.1 ml of methanol. To the solution which was placed on a steam-bath, 100 ml of ethyl acetate was added and the resulting cloudy solution was continuously heated to distill 25–30 ml of methylene chloride. The mixture was cooled, and the white precipitated solid was filtered to afford 6,11-ethano-12-ethylene-6,11-dihydrobenzo[b]quinolizinium bromide (Example 13(a)) (Formula I: $R^1=R^2=R^3=R^4=H;R^5=CH_2=CH—;X^-=Br^-$); isomer A, as a white powder.

The Fraction B was concentrated in vacuo and the residue was triturated with methylene chloride/ethyl acetate. The product was isolated and dried at 60° C. under diminished pressure to afford 6,11-ethano-12-ethylene6,11-dihydrobenzo[b]quinolizinium bromide (Example 13(b)) (Formula I: $R^1=R^2=R^3=R^5=H;R^4=CH_2=CH—;X^-=Br^-$), isomer B.

EXAMPLE 14

Following a procedure similar to that described in Example 2, a reaction mixture of 5 g (16.3 mmol) of benzo[b]quinolizinium hexafluorophosphate and 3.6 g (32 mmol) of 1,5-dimethyl-2,4-hexadiene in 50 ml of nitromethane was heated to reflux for 6 hours. After adding an additional 5 ml of 1,5-dimethyl-2,4-hexadiene, the reaction mixture was allowed to reflux for 12 hours and then cooled. The reaction mixture was treated with one teaspoonful of activated charcoal with stirring (5 minutes) and filtered through celite. The filtrate was concentrated in vacuo and the yellow foamy residue was dissolved in a small amount of methanol. The above methanolic solution was triturated with 100 ml of hot (70° C.) water, a solid product was filtered and dried (40° C.) under diminished pressure to afford as a mixture of geometrics isomers 6.3 g (88.8%) of 6,11-ethano-12-(2,2-dimethyl)ethylene-13,13-dimethyl-6,11-dihydrobenzo[b]quinolizinium hexafluorophosphate (Formula I: $R^1H;R^2=R^3=CH_3;R^4=H;R^5=(CH_3)_2C=CH—;X^-=PF_6^-$; and Formula I: $R^1H; R^2=R^3=CH_3;R^4=(CH_3)_2C=CH—;R^5=H;X^-=PF_6^-$), m.p. 95°–99° C.

EXAMPLE 15

(a)

Following a procedure similar to that described in Example 2, 1.48 g (10 mmol) of 2-methyleneadamantane was added to 25 ml of nitromethane containing 1.4 g (5 mmol) of benzo[b]quinolizinium perchlorate and the reaction mixture was allowed to reflux under argon with stirring for 36 hours. The solvent was removed in vacuo, a green residue was triturated with ether, and the solid was filtered to afford 2.1 g (100%) of 6,11-ethano-12,12-(2'-spiroadamantane)- 6,11-dihydrobenzo[b]quinolizinium perchlorate (Formula I: $R^1=R^2=R^3=H;R^4$ and $R^5$ together are adamantanyl;$X^-=ClO_4^-$).

(b)

The above perchlorate (2.1 g) was passed through Dowex®1×2-200 eluting with water and the solvent was concentrated in vacuo to yield a glass (1.4 g). The product was recrystallized from isopropanol/isopropyl acetate to afford 1.2 g (66%) of 6,11-ethano-12,12-(2'-spiro-adamantane)-6,11-dihydrobenzo[b]quinolizinium chloride (Formula I: $R^1=R^2=R^3=H;R^4$ and $R^5$ together are adamantanyl;$X^-=Cl^-$), m.p.>320° C.

EXAMPLE 16

A mixture of benzo[b]quinolizinium perchlorate (1.9 g, 0.0069 mol), nitromethane (20 mL) and tetramethylallene (1.0 g, 0.010 mol) was heated to reflux for 12 hours, additional tetramethylallene (1.0 g) was added and heating was continued for 2 more hours. The solvent was removed in vacuo, the residue was taken up in hot isopropanol, the solution was cooled, and the precipitate which formed was collected by filtration to afford 1.8 g of a 1.85 to 1 mixture of 12-isopropylidene-13,13-dimethyl-6,11-ethano-6,11-dihydrobenzo[b]quinolizinium perchlorate (Formula I: $R^1$=H;$R^2$=$R^3$=CH$_3$;$R^4$ and $R^5$ together =isopropylidene;$X^-$=ClO$_4^-$) and 12,12-dimethyl-13-isopropylidene-6,11-ethano-6,11-dihydrobenzo[b]quinolizinium perchlorate (Formula I: $R^1$=H;$R^2$ and $R^3$ together=isopropylidene;$R^4$=$R^5$=CH$_3$;$X^-$= ClO$_4^-$).

EXAMPLE 17

(a)

A mixture of benzo[b]quinolizinium perchlorate (3.0 g, 10.73 mmol), nitromethane (50 mL) and 2,2-(diethoxymethylethylene (2.8 g, 19.44 mmol) was refluxed for 48 hours. The solvent was removed in vacuo, the residue was triturated with methylene chloride and the resulting solid was collected by filtration. The filtrate was concentrated in vacuo and the residue was purified by column chromatography on silica gel eluting with CH$_2$Cl$_2$/methanol (20/1) to afford 1.5 g (33%) of 12,12-diethoxymethyl-6,11-ethano-6,11-dihydrobenzo[b]quinolizinium perchlorate (Formula I: $R^1$=$R^2$=$R^3$—=H;$R^4$=$R^5$=CH$_2$OC$_2$H$_5$;$X^-$=ClO$_4^-$).

(b)

The latter (1.5 g, 5.54 mmol) was passed through a Dowex®1×2-200 ion exchange resin column eluting with water to afford 0.83 g of 12,12-diethoxymethyl-6,11-ethano-6,11-dihydrobenzo[b]quinolizinium chloride (Formula I: $R^1$=$R^2$=$R^3$=H;$R^4$=$R^5$=CH$_2$OC$_2$H$_5$;$X^-$=Cl$^-$).

EXAMPLE 18

(a)

To a mixture of benzo[b]quinolizinium hexafluorophosphate (0.428 g, 0.0014 mol), nitromethane, (25 mL) and pyridinium p-toluenesulfonate (0.1 g) was added 2,2-di-[2-(trimethylsilyl)ethynyl]ethanol (0.5 g, 0.02 mol) (forms 2,2-di[2-(trimethylsilyl)ethynyl]ethylene in situ). The mixture was heated to reflux for 12 hours, cooled and filtered. The solvent was removed in vacuo, and the residue was diluted with ether and the ether was decanted. The residue was purified by column chromatography on silica gel eluting with E/PAW (1.5/1) to afford the product which was recrystallized from hot isopropanol to afford 0.163 g of 12,12-di(2-trimethylsilylethyne)-6,11-ethano-6,11-dihydrobenzo[b]quinolizinium hexafluorophosphate.

(b)

To a solution of the latter (0.05 g) in methanol (10 mL) was added K$_2$CO$_3$ (0.05 g), followed 10 minutes later by 10% aqueous K$_2$CO$_3$ (15 mL). When the reaction was complete, the mixture was extracted with CH$_2$Cl$_2$, and the organic layer was dried over Na$_2$SO$_4$, filtered and concentrated in vacuo. The residue was recrystallized from hot isopropanol to afford 0.3 g of 12,12-diethynyl-6,11-ethano-6,11-dihydrobenzo[b]quinolizinium hexafluorophosphate (Formula I: $R^1$=$R^2$=$R^3$=H;$R^4$=$R^5$=—C≡CH;$X^-$=PF$_6^-$), m.p. 96°–99° C.

EXAMPLE 19

A mixture of benzo[b]quinolizinium hexafluorophosphate (0.311 g), nitromethane (3 mL) and 3-methyl-2-isopropyl-1-butene (0.336 g) was heated at 125°–130° C. for 24 hours. The solvent was removed in vacuo, the residue was stirred with ethyl acetate and the product was collected by filtration to afford 0.110 g of 12,12-diisopropyl-6,11-dihydrobenzo[b]quinolizium hexafluorophosphate (Formula I: $R^1$=$R^2$=$R^3$=H;$R^4$=$R^5$=CH(CH$_3$)$_2$;$X^-$=PF$_6^-$), m.p. 204°–206° C. (dec).

Following procedures similar to those described hereinabove, or by utilizing procedures which are known in the art, the following known compound (Example 20) was prepared and, unexpectedly, was found to bind to the PCP receptor and is thus useful in the treatment or prevention of neurodegenerative disorders or neurotoxic injuries.

EXAMPLE 20

6,11-ethano-12-isopropenyl-12-methyl-6,11-dihydrobenzo[b]quinolizinium perchlorate as a mixture of geometric isomers (Formula I: $R^1$=$R^2$=$R^3$=H;$R^4$=CH$_2$=C(CH$_3$)—;$R^5$=CH$_3$;$X^-$=ClO$_4^-$ and Formula I: $R^1$=$R^2$=$R^3$=H;$R^4$=CH$_3$; $R^5$=CH$_2$=C(CH$_3$)—;$X^-$=ClO$_4^-$).

BIOLOGICAL TEST RESULTS

Representative examples of the compounds of the invention have been found to possess valuable pharmacological properties. In particular, they have been found to bind to the PCP receptor and are thus non-competitive blockers (antagonists) of the effects which excitatory amino acids, such as glutamate, have upon the NMDA receptor. The compounds of the invention are thus useful in the treatment of neurodegenerative disorders such as Huntington's disease, Alzheimer's disease, amyotrophic lateral sclerosis, Down's Syndrome, senile dementia, glutaric acidaemia type I, multi-infarct dementia, Parkinson's disease, viral encephalopathies (which include, but are not limited thereto, dementia associated with HIV infections) and neuronal damage associated with uncontrolled seizures, as well as in the treatment or prevention of neurotoxic injuries associated with ischemic, hypoxic; or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, spinal or head trauma, neonatal anoxic trauma, coronary artery bypass graft, and perinatal asphyxia.

The compounds of the invention are particularly useful in the treatment or prevention of neurotoxic injuries associated with ischemic, hypoxic; or hypoglycemic conditions, and especially ischemic, hypoxic, or hypoglycemic conditions which are associated with stroke.

The pharmacological properties of representative examples of the compounds of the invention was demonstrated by conventional in vitro biological test procedures such as the following:

[³H]TCP Radioreceptor Assay (internal screen)

[³H]TCP binding to PCP recognition sites was performed as described by Vignon et al. Brain Research 1983, 280, 194–197. Male Sprague-Dawley rats were sacrificed by decapitation, and whole brains were homogenized in 10 volumes (wt/vol) of cold Tris-HCl buffer (50 mM, pH 7.7) using a Brinkmann Polytron (setting 6, 30 sec). The homogenate was centrifuged at 40,000×g for 10 min at 4° C. The supernatant was decanted, and the homogenization and centrifugation steps were repeated twice as described above. Following this, the pellet was resuspended in Tris-HCl (5 mM, pH 7.7) at a tissue concentration of 0.5–0.75 g/ml, and one ml aliquots were frozen at −70° C. until use. The binding characteristics for PCP recognition sites were not altered by the freezing of membrane suspensions.

On the day of the assay, membrane aliquots were thawed, resuspended in fresh 5 mM Tris-HCl buffer at a tissue concentration of 1 mg/ml, and stored on ice until use. Each assay tube contained 100 μl of [$^3$H]TCP at a final concentration of approximately 1 nM, 100 μl of various concentrations of the compounds of interest, 500 μl of the tissue suspension and 300 μl of buffer to a final assay volume of 1 ml and a final protein concentration of 0.5 mg/tube. Nonspecific binding was defined by addition of a final concentration of 100 μM to blank tubes. All tubes were incubated at room temperature for 25 min before termination of the reaction by rapid filtration over Whatman GF/B glass fiber filters that had been presoaked in a solution of 0.5% polyethylenimine for at least 1 hr prior to use. Filters were washed with three 4 ml volumes of cold Tris buffer. Following addition of scintillation cocktail, the amount of bound radioactivity was determined by liquid scintillation spectrometry using a Beckman LS 5000TA liquid scintillation counter with an efficiency for tritium of approximately 55%. Inhibition constants ($K_i$ values) were calculated using the EBDA/LIGAND program (McPherson, J. Pharmacol. Meth. 1985, 14, 213–228), purchased from Elsevier/Biosoft, Inc. Results are reported as $K_i$ values which are expressed as the mean of at least two separate determinations, or as a percent (%) inhibition of binding at 10 μM.

Representative compounds of the invention were also tested in an external [$^3$H]TCP radioreceptor assay using the following protocol:

[$^3$H]TCP Radioreceptor Assay (external screen)

A procedure similar to that described above for the [$^3$H]TCP radioreceptor assay (internal screen) was utilized except that the whole rat forebrain membranes were incubated at 25° C. for 60 minutes rather than at room temperature for 25 minutes, before termination of the reaction. The results are reported as a percent (%) inhibition of binding at 10 μM.

Antagonism of NMDA-induced Neurotoxicity in Cultured Neurons

Preparation of cultured cortical neurons

Pregnant, Swiss-Webster mice were obtained from Taconic Farms (Germantown, N.Y.) and sacrificed 16 days post conception. Fetuses were removed and placed in a sterile dish containing Hank's balanced salt solution (HBSS), pH 7.4. Brain cortices were dissected, meninges were removed, the tissue was minced and placed into a solution of HBSS containing 0.25% (w/v) trypsin at 37° C. for 15 minutes. Tissue was then triturated with a sterile pasteur pipet, diluted with minimal essential media (Gibco 330–1430), pH 7.4, supplemented with 10% horse serum, 10% fetal calf serum, 2 mM l-glutamine, 21 mM d-glucose, 2.2 g/L sodium bicarbonate, 1000 U/ml penicillin, and 1,000 μg/ml streptomycin. Cells were plated onto Falcon primaria 96 well plates at a final density of 50,000 cells/well and incubated at 37° C. in the presence of 5% (v/v) carbon dioxide. After 5 days, plating media was replaced with maintenance media containing minimal essential media (Gibco 330–1430), pH 7.4, supplemented with 10% horse serum, 10% l-glutamine, 21 mM d-glucose, 2.2 g/l sodium bicarbonate, 1,000 U/ml penicillin, 1,000 μg/ml streptomycin, and 10 μM cytosine arabinoside. On days 7 and 10, media was replaced with maintenance media as above lacking the cytosine arabinoside. Experiments were conducted on day 13.

Neuroprotection Assessment

Day 13 cultured cortical neurons were washed twice with minimal essential media, pH 7.4 and then exposed for 30 minutes to 500 μM N-methyl-D-aspartic acid (NMDA) with or without varying concentrations of test agents. Dizocilpine (MK-801) at a final concentration of 10 μM MK-801 was routinely included as a positive control. MK-801 and test agents were prepared in minimal essential media supplemented with 21 mM d-glucose and 2.2 g/L sodium bicarbonate (MEM). After 30 minutes, media was replaced with MEM alone. Exposure of neurons to test agents was limited to the NMDA treatment period. Twenty-four hours after removal of NMDA, an aliquot of media from each well was removed for assessment of cell injury by determining lactate dehydrogenase (LDH) activity by the method of Wroblewski and LaDue Proc. Soc. Exp. Biol. Med. 1955, 90, 210–213. The results are expressed as an $IC_{50}$ (in nM) value (concentration causing 50% inhibition) for the antagonism of NMDA—induced neurotoxicity.

Table 1 summarizes the results obtained from the testing of representative compounds of the invention in the [$^3$H] TCP radioreceptor assay (internal screen and external screen) as well as in the antagonism of NMDA—induced neurotoxicity in cultured neurons.

TABLE 1

| Example Number | [$^3$H]TCP (internal screen) $K_i$(nM) or Percent (%) inhibition @10 μM | [$^3$H]TCP (external screen) Percent inhibition (%) @10 μM | Antagonism of NMDA-induced neurotoxicity ($IC_{50}$ in nM) |
|---|---|---|---|
| 1 | 21.2 | — | — |
| 2 | 208 | — | 7300 |
| 3 | 191 | — | 5880 |
| 4 | 313 | — | — |
| 5 | 65.2 | — | 2812 |
| 6 | 44% | — | — |
| 7 | 5088 | — | — |
| 8 | 88.1 | — | — |
| 9 | 103 | — | — |
| 10(b) | 3108 | — | — |
| 11(b) | 1948 | — | — |
| 12 | 69.0 | — | — |
| 13(a) | 49% | — | — |
| 14 | 3541 | — | — |
| 15(b) | 5285 | — | — |
| 16 | 265 | — | — |
| 17(b) | 353 | — | — |
| 18(b) | 883 | — | — |
| 19 | 6010 | — | — |
| 20 | 45.7 | 94% | — |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

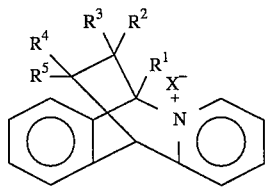

wherein:

$R^1$ is hydrogen, or $C_1-C_4$ alkyl;

$R^2$ is hydrogen, or $C_1-C_4$ alkyl;

$R^3$ is hydrogen, or $C_1-C_4$ alkyl; or $R^2$ and $R^3$ together are $C_1-C_4$ alkylidene;

$R^4$ is hydrogen, $C_1-C_4$ alkyl, $C_2-C_4$ alkenyl, $C_1-C_4$ alkoxy-$C_1-C_4$ alkyl, $C_3-C_7$ cycloalkyl, hydroxy-$C_1-C_4$ alkyl or $C_2-C_4$ alkynyl;

$R^5$ is hydrogen, $C_1-C_4$ alkyl, $C_2-C_4$ alkenyl, $C_3-C_7$ cycloalkyl, hydroxy- $C_1-C_4$ alkyl, $C_1-C_4$ alkoxy-$C_1-C_4$ alkyl or $C_2-C_4$ alkynyl; or $R^4$ and $R^5$ together form a $C_1-C_4$ alkylidene, $C_3-C_7$ cycloalkyl, or adamantanyl group; and $X^-$ is an anion selected from the group consisting of acetic acid, methanesulfonic acid, toluenesulfonic acid, chloride, bromide and perchlorate;

or a stereoisomer thereof; with the following provisos:

a) when $R^1$, $R^2$, and $R^3$ are hydrogen; $R^4$ is methyl; and $X^-$ is $Br^-$, $Cl^-$, or $ClO_4^-$, $R^5$ cannot be isopropenyl; b) when $R^1$, $R^2$, and $R^3$ are hydrogen; $R^5$ is methyl; and $X^-$ is $Br^-$, $Cl^-$, or $ClO_4^-$, $R^4$ cannot be isopropenyl; c) $R^1$, $R^2$, $R^3$, $R^4$ and $R^5$ cannot all simultaneously be hydrogen; d) when $R^1$, $R^2$, and $R^3$ are hydrogen; $X^-$ is $Br^-$, and either, $R^4$ or $R^5$, but not both, is hydrogen; then either $R^4$ or $R^5$ cannot be ethenyl, hydroxymethyl, or ethyl and e) when $R^2$, $R^3$, $R^4$ or $R^5$ are a $C_1-C_4$ alkyl group other than methyl, at least two of $R^2$, $R^3$, $R^4$ and $R^5$ must be hydrogen.

2. A compound according to claim 1 wherein $R^1$ is hydrogen or methyl.

3. A compound according to claim 2 wherein $R^2$ is hydrogen, methyl or tert-butyl; $R^3$ is hydrogen, methyl or tert-butyl, or $R^2$ and $R^3$ together are isopropylidene.

4. A compound according to claim 3 wherein $R^4$ is hydrogen, methyl, isopropyl, tert-butyl, isopropenyl, isobutenyl, methoxymethyl, cyclopropyl, hydroxymethyl, ethoxymethyl, or ethynyl; $R^5$ is hydrogen, methyl, isopropyl, tert-butyl, isopropenyl, isobutenyl, cyclopropyl, hydroxymethyl, ethoxymethyl, or ethynyl; or $R^4$ or $R^5$ together form a isopropylidene, cyclobutyl, or adamantanyl group, and $X^-$ is anion selected from the group consisting of acetic acid, methanesulfonic acid, toluenesulfonic acid, chloride, bromide and perchlorate.

5. 12,12,13,13-tetramethyl-6,11-ethano-6,11-dihydrobenzo[b]quinolizinium perchlorate according to claim 4.

6. A pharmaceutical composition for blocking the effects of excitatory amino acids upon the NMDA receptor in a mammal which comprises an effective blocking amount of a compound of the formula

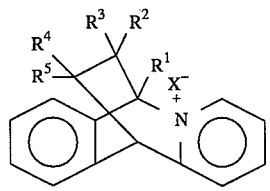

wherein:

$R^1$ is hydrogen, or $C_1-C_4$ alkyl;

$R^2$ is hydrogen, or $C_1-C_4$ alkyl;

$R^3$ is hydrogen, or $C_1-C_4$ alkyl; or $R^2$ and $R^3$ together are $C_1-C_4$ alkylidene;

$R^4$ is hydrogen, $C_1-C_4$ alkyl, $C_2-C_4$ alkenyl, $C_1-C_4$ alkoxy-$C_1-C_4$ alkyl, $C_3-C_7$ cycloalkyl, hydroxy-$C_1C_4$ alkyl or $C_2-C_4$ alkynyl;

$R^5$ is hydrogen, $C_1-C_4$ alkyl, $C_2-C_4$ alkenyl, $C_3-C_7$ cycloalkyl, hydroxy-$C_1-C_4$ alkyl, $C_1-C_4$ alkoxy-$C_1-C_4$ alkyl or $C_2-C_4$ alkynyl; or $R^4$ and $R^5$ together form a $C_1-C_4$ alkylidene, $C_3-C_7$ cycloalkyl, or adamantanyl group; and X⁻ is an anion selected from the group consisting of acetic acid, methanesulfonic acid. toluenesulfonic acid, chloride, bromide and perchlorate;

or a stereoisomer thereof; with the following provisos:
a) when $R^1$, $R^2$, and $R^3$ are hydrogen; $R^4$ is methyl; and X⁻ is Br⁻, Cl⁻, or $ClO_4^-$, $R^5$ cannot be isopropenyl; b) when $R^1$, $R^2$, and $R^3$ are hydrogen; $R^5$ is methyl; and X⁻ is Br⁻, Cl⁻, or $ClO_4^-$, $R^4$ cannot be isopropenyl; c) $R^1$, $R^2$, $R^3$, $R^4$ and $R^5$ cannot all simultaneously be hydrogen; d) when $R^1$, $R^2$, and $R^3$ are hydrogen; X⁻ is Br⁻, and either, $R^4$ or $R^5$, but not both, is hydrogen; then either $R^4$ or $R^5$ cannot be ethenyl, hydroxymethyl, or ethyl and e) when $R^2$, $R^3$, $R^4$ or $R^5$ are a $C_1$–$C_4$ alkyl group other than methyl, at least two of $R^2$, $R^3$, $R^4$ and $R^5$ must be hydrogen.

7. A pharmaceutical composition according to claim 6 wherein $R^1$ is hydrogen or methyl; $R^2$ is hydrogen, methyl, or tert-butyl; $R^3$ is hydrogen, methyl, or tert-butyl; or $R^2$ and $R^3$ together are isopropylidene.

8. A pharmaceutical composition according to claim 7 wherein $R^4$ is hydrogen, methyl, isopropyl, tert-butyl, isopropenyl, isobutenyl, methoxymethyl, cyclopropyl, hydroxymethyl, ethoxymethyl, or ethynyl; $R^5$ is hydrogen, methyl, isopropyl, tert-butyl, isopropenyl, isobutenyl, ethenyl, cyclopropyl, hydroxymethyl, ethoxymethyl, or ethynyl; or $R^4$ and $R^5$ together form a isopropylidene, cyclobutyl, or adamantanyl group; and X⁻ is anion selected from the group consisting of acetic acid, methanesulfonic acid, toluenesulfonic acid, chloride, bromide and perchlorate.

9. A pharmaceutical composition according to claim 8 wherein the compound is 12,12,13,13-tetramethyl-6,11-ethano-6,11-dihydrobenzo[b]quinolizinium perchlorate.

10. A method for treatment of ischemic, hypoxic or hypoglycemic conditions which comprises administering to a patient in need of such treatment an ischemic, hypoxic or hypoglycemic treating effective amount of a compound of the formula:

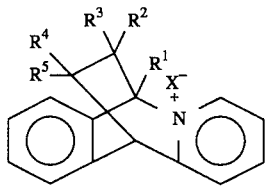

wherein:
$R^1$ is hydrogen, or $C_1$–$C_4$ alkyl;

$R^2$ is hydrogen, or $C_1$–$C_4$ alkyl;

$R^3$ is hydrogen, or $C_1$–$C_4$ alkyl; or $R^2$ and $R^3$ together are $C_1$–$C_4$ alkylidene;

$R^4$ is hydrogen, $C_1$–$C_4$ alkyl, $C_2$–$C_4$ alkenyl, $C_1$–$C_4$ alkoxy-$C_1$–$C_1C_4$ alkyl, $C_3$–$C_7$ cycloalkyl, hydroxy-$C_1$–$C_4$ alkyl or $C_2$–$C_4$ alkynyl;

$R^5$ is hydrogen, $C_1$–$C_4$ alkyl, $C_2$–$C_4$ alkenyl, $C_3$–$C_7$ cycloalkyl, hydroxy-$C_1$–$C_4$ alkyl, $C_1$–$C_4$ alkoxy-$C_1$–$C_4$ alkyl or $C_2$–$C_4$ alkynyl; or $R^4$ and $R^5$ together form a $C_1$–$C_4$ alkylidene, $C_3$–$C_7$ cycloalkyl, or adamantanyl group; and X⁻ is an anion selected from the group consisting of acetic acid, methanesulfonic acid, toluenesulfonic acid, chloride, bromide and perchlorate;

or a stereoisomer thereof; with the following proviso that:
a) $R^1$, $R^2$, and $R^3$ and $R^4$ cannot all simultaneously be hydrogen; and further provided that when $R^1$, $R^2$, and $R^3$ are hydrogen, X⁻ is Br⁻ and either $R^4$ or $R^5$, but not both, is hydrogen, then either $R^4$ or $R^5$ cannot be ethyl.

11. A method according to claim 10 wherein $R^1$ is hydrogen or methyl; $R^2$ is hydrogen, methyl, or tert-butyl; $R^3$ is hydrogen, methyl, or tert-butyl; or $R^2$ and $R^3$ together are isopropylidene.

12. A method according to claim 11 wherein $R^4$ is hydrogen, methyl, isopropyl, tert-butyl, isopropenyl, isobutenyl, methoxymethyl, cyclopropyl, hydroxymethyl, ethoxymethyl, or ethynyl; $R^5$ is hydrogen, methyl, isopropyl, tert-butyl, isopropenyl, isobutenyl, ethenyl, cyclopropyl, hydroxymethyl, ethoxymethyl, or ethynyl; or $R^4$ and $R^5$ together form a isopropylidene, cyclobutyl, or adamantanyl group; and X⁻ is an anion selected from the group consisting of acetic acid, methanesulfonic acid, toluenesulfonic acid, chloride, bromide and perchlorate.

13. A method according to claim 12 wherein the compound is 12,12,13,13-tetramethyl-6,11-ethano-6,11-dihydrobenzo[b]quinolizinium perchlorate.

14. A method according to claim 10 for the treatment of hypoxic conditions.

15. A method according to claim 14 for the treatment of hypoglycemic conditions.

16. A method according to claim 10 for the treatment of ischemic conditions.

* * * * *